US011413264B2

(12) United States Patent
Hurley

(10) Patent No.: US 11,413,264 B2
(45) Date of Patent: Aug. 16, 2022

(54) CARBAMOYL PHENYLALANINOL ANALOGS AND USES THEREOF

(71) Applicant: Jazz Pharmaceuticals Ireland Limited, Dublin (IE)

(72) Inventor: Fionn Hurley, Baldoyle (IE)

(73) Assignee: Jazz Pharmaceuticals Ireland Limited, Dublin (IE)

(*) Notice: Subject to any disclaimer, the term of this patent is extended or adjusted under 35 U.S.C. 154(b) by 170 days.

(21) Appl. No.: 16/634,935

(22) PCT Filed: Jul. 31, 2018

(86) PCT No.: PCT/US2018/044465
§ 371 (c)(1),
(2) Date: Jan. 29, 2020

(87) PCT Pub. No.: WO2019/027941
PCT Pub. Date: Feb. 7, 2019

(65) Prior Publication Data
US 2021/0093603 A1     Apr. 1, 2021

Related U.S. Application Data

(60) Provisional application No. 62/539,088, filed on Jul. 31, 2017.

(51) Int. Cl.
| A61K 31/27 | (2006.01) |
| A61K 31/165 | (2006.01) |
| A61K 31/17 | (2006.01) |
| A61K 31/255 | (2006.01) |
| C07C 233/11 | (2006.01) |
| C07C 275/24 | (2006.01) |
| C07C 307/02 | (2006.01) |
| C07C 333/04 | (2006.01) |

(52) U.S. Cl.
CPC ............ *A61K 31/27* (2013.01); *A61K 31/165* (2013.01); *A61K 31/17* (2013.01); *A61K 31/255* (2013.01); *C07C 233/11* (2013.01); *C07C 275/24* (2013.01); *C07C 307/02* (2013.01); *C07C 333/04* (2013.01)

(58) Field of Classification Search
CPC .................................................... A61K 31/27
See application file for complete search history.

(56) References Cited

U.S. PATENT DOCUMENTS

| 5,705,640 A | 1/1998 | Choi et al. |
| 5,756,817 A | 5/1998 | Choi et al. |
| 5,935,997 A | 8/1999 | Choi et al. |
| 5,955,499 A | 9/1999 | Choi et al. |
| 6,140,532 A | 10/2000 | Choi et al. |
| 6,680,299 B2 | 1/2004 | Or et al. |
| 6,680,322 B2 | 1/2004 | Castelhano et al. |
| 6,680,324 B2 | 1/2004 | Castelhano et al. |
| 8,232,315 B2 | 7/2012 | Lee et al. |
| 8,440,715 B2 | 5/2013 | Ahnaou et al. |
| 8,552,060 B2 | 10/2013 | Palumbo et al. |
| 8,623,913 B2 | 1/2014 | Melnick et al. |
| 8,729,120 B2 | 5/2014 | Sporn |
| 8,741,950 B2 | 6/2014 | Khayrallah et al. |
| 8,895,609 B2 | 11/2014 | Lee et al. |
| 8,927,602 B2 | 1/2015 | Lee et al. |
| 8,952,062 B2 | 2/2015 | Cook et al. |
| 9,050,302 B2 | 6/2015 | Eller |
| 9,226,910 B2 | 1/2016 | Khayrallah et al. |
| 9,359,290 B2 | 6/2016 | Khayrallah et al. |
| 9,610,274 B2 | 4/2017 | Lee et al. |
| 10,195,151 B2 | 2/2019 | Allphin et al. |
| 2015/0018414 A1 | 1/2015 | Khayrallah et al. |
| 2019/0218175 A1 | 7/2019 | Hurley et al. |

FOREIGN PATENT DOCUMENTS

| CN | 101823987 | 9/2010 |
| CN | 102249833 | 11/2011 |
| CN | 102249833 A | 11/2011 |
| JP | H01501227 A | 4/1989 |
| JP | 2002536358 A | 10/2002 |
| JP | 2006524216 A | 10/2006 |
| WO | 1998/017636 | 4/1998 |
| WO | 2000/046191 | 8/2000 |
| WO | 0044770 A1 | 8/2000 |
| WO | 0064865 A1 | 11/2000 |
| WO | 2002/100804 | 12/2002 |
| WO | 2017/007695 | 1/2017 |

OTHER PUBLICATIONS

Gros et al. "Potent Inhibition of Cerebral Aminopeptidases by Carbaphethiol, A Parenterally Active Compound" Neuropeptides 12, 111-118 (1988).
International Search Report and Written Opinion corresponding to International Application No. POT/US2018/044465 dated Nov. 8, 2018.
Phenprobamate, Wikipedia, https://en.wikipedia.org/wiki/Phenprobamate, last edited Apr. 2, 2016, accessed Sep. 24, 2019.
International Preliminary Report on Patentability corresponding to International Application No. PCT/US2018/044465 dated Feb. 13, 2020.
"Office Action corresponding to Russian Application No. 2020108634 dated Nov. 30, 2021".
Belikov, V. G, "Pharmaceutical Chemistry", chapter 2.6 "Communication between the chemical structure, properties of substances and their effect on the body", MEDpress-inform, Moscow, 2007, pp. 27-29.
"Office Action corresponding to Australian Application No. 2018312328 dated Dec. 1, 2021".
"Office Action corresponding to Indian Application No. 202017008027 dated Sep. 24, 2021".

(Continued)

*Primary Examiner* — Svetlana M Ivanova
(74) *Attorney, Agent, or Firm* — Myers Bigel, P.A.

(57) ABSTRACT

The present invention relates to carbamoyl phenylalaninol analogs and methods of using the same to treat disorders.

12 Claims, No Drawings

(56) References Cited

OTHER PUBLICATIONS

"Extended European Search Report corresponding to European Application No. 18840981.7 dated Mar. 12, 2021".
Registry (STN) [online] Aug. 25, 2004 [Search Date: Mar. 24, 2022] CAS Registration No. 732233-83-9.
Registry (STN) [online] Dec. 8, 2004 [Search Date Mar. 24, 2022] CAS Registration No. 794507-90-7.
Registry (STN) [online] Dec. 8, 2004 [Search Date Mar. 24, 2022] CAS Registration No. 794507-91-8.
Registry (STN) [online] May 31 2004 [Search Date: Mar. 24, 2022] CAS Registration No. 687995-04-6.
Registry (STN) [online] Nov. 30, 2004 [Search Date Mar. 24, 2022] CAS Registration No. 790644-78-9.
Registry (STN) [online] Oct. 7, 2004 [Search Date Mar. 24, 2022] CAS Registration No. 757927-89-2.
Registry (STN) [online] Oct. 26, 2004 [Search Date Mar. 24, 2022] CAS Registration No. 769907-08-6.
Registry (STN) [online] Oct. 29, 2004 [Search Date Mar. 24, 2022] CAS Registration No. 772325-14-1.
Registry (STN) [online] Sep. 10, 2004 [Search Date Mar. 24, 2022] CAS Registration No. 736915-57-4.
Registry (STN) [online] Sep. 27, 2004 [Search Date Mar. 24, 2022] CAS Registration No. 752969-88-3.
Registry (STN) [online], Aug. 27, 2004 [Search Date Mar. 24, 2022] CAS Registration No. 733727-20-3.
Registry (STN) [online], Jul. 28, 2004 [Search Date: Mar. 24, 2022] CAS Registration No. 718595-82-5.
"Office Action corresponding to Japanese Application No. 2020-505344 dated May 10, 2022".
"Office Action corresponding to Mexican Application No. MX/a/2020/001146 dated May 3, 2022".
"Office Action corresponding to Russian Application No. 2020108634 dated Apr. 25, 2022".
"Office Action corresponding to Saudi Arabian Application No. 520411187 dated Apr. 2, 2022".
Piper, James, et al., "The Use of Alpha-Amino Acids in the Synthesis of Derivatives of 2-Aminoethanethiol as Potential Antiradiation Agents", Journal of Medicinal Chemistry 9(6):911-920 (Nov. 1966).

CARBAMOYL PHENYLALANINOL ANALOGS AND USES THEREOF

STATEMENT OF PRIORITY

This application is a 35 U.S.C. § 371 national phase plication of PCT Application PCT/US2018/044465 filed Jul. 31, 2018 which claims the benefit, under 35 U.S.C. § 119(e), of U.S. Provisional Application No. 62/539,088, filed Jul. 31, 2017, the entire contents of each of which are incorporated by reference herein in its entirety.

FIELD OF THE INVENTION

The present invention relates to carbamoyl phenylalaninol analogs and methods of using the same to treat disorders.

BACKGROUND OF THE INVENTION (R)-2-amino-3-phenylpropyl carbamate (APC) is a phenylalanine analog that has been demonstrated to be useful in the treatment of a variety of disorders, including excessive daytime sleepiness, cataplexy, narcolepsy, fatigue, depression, bipolar disorder, fibromyalgia, and others. See, for example, U.S. Pat. Nos. 8,232,315; 8,440,715; 8,552,060; 8,623,913; 8,729,120; 8,741,950; 8,895,609; 8,927,602; 9,226,910; and 9,359,290; and U.S. Publication Nos. 2012/0004300 and 2015/0018414. Methods for producing APC (which also has other names) and related compounds can be found in U.S. Pat. Nos. 5,955,499; 5,705,640; 6,140,532 and 5,756,817. All of the above patents and applications are hereby incorporated by reference in their entireties for all purposes.

The present invention overcomes shortcomings in the art by providing analogs of APC and a method of using the same to treat disorders.

SUMMARY OF THE INVENTION

The present invention relates to the development of analogs of APC with similar pharmacological activities. Accordingly, the present invention relates to a compound of Formula I:

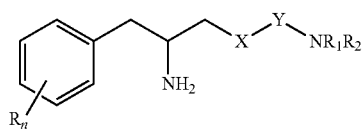

I or a pharmaceutically acceptable salt thereof, wherein:
X is $CH_2$, O, NH, or S;
Y is C=O, C=S, or $SO_2$;
R is optionally substituted $C_{1-8}$ alkyl, halogen, optionally substituted $C_{1-4}$ alkoxy, cyano, hydroxy, optionally substituted trifluoromethyl, or $C_{1-4}$ thioalkoxy;
n is 0, 1, 2, or 3, with the proviso that R may be the same or different when x is 2 or 3; and
$R_1$ and $R_2$ can be the same or different and are independently selected from the group consisting of hydrogen, optionally substituted $C_{1-8}$ alkyl, optionally substituted amide, optionally substituted aryl, optionally substituted heteroaryl, optionally substituted arylalkyl, and optionally substituted $C_{3-7}$ cycloalkyl;

or $R_1$ and $R_2$ can be joined to form a 5 to 7-membered heterocycle optionally substituted with alkyl or aryl groups, wherein the cyclic compound can comprise 1 to 2 nitrogen atoms and 0 to 1 oxygen atom, wherein the nitrogen atoms are not directly connected with each other or with the oxygen atom;
wherein when Y is C=O, X is not O.

Another aspect of the invention relates to a composition (e.g., a pharmaceutical composition) and kit comprising the compound of the invention.

A further aspect of the invention relates to a method of treating a disorder or condition selected from narcolepsy, cataplexy, excessive daytime sleepiness, drug addiction, sexual dysfunction, fatigue, fibromyalgia, attention deficit/hyperactivity disorder, restless legs syndrome, depression, bipolar disorder, atypical depression, freezing of gait, mild cognitive impairment, neurogenic orthostatic hypertension, binge eating disorder, or obesity in a subject in need thereof, or promoting smoking cessation in a subject in need thereof, comprising administering to the subject a therapeutically effective amount of a compound of the invention, thereby treating the disorder or condition or promoting smoking cessation.

The present invention is explained in greater detail in the drawings herein and the specification set forth below.

DETAILED DESCRIPTION OF THE INVENTION

The present invention can be embodied in different forms and should not be construed as limited to the embodiments set forth herein. Rather, these embodiments are provided to exemplify aspects of the invention as representatives of the full scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Unless the context indicates otherwise, it is specifically intended that the various features of the invention described herein can be used in any combination.

Moreover, the present invention also contemplates that in some embodiments of the invention, any feature or combination of features set forth herein can be excluded or omitted.

To illustrate, if the specification states that a complex comprises components A, B and C, it is specifically intended that any of A, B or C, or a combination thereof, can be omitted and disclaimed singularly or in any combination.

All publications, patent applications, patents, and other references mentioned herein are incorporated by reference herein in their entirety for all purposes.

As used herein, "a," "an," or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±10%, ±5%, ±1%, ±0.5%, or even ±0.1% of the specified amount.

The term "consists essentially of" (and grammatical variants), as applied to the compositions of this invention, means the composition can contain additional components as long as the additional components do not materially alter the composition. The term "materially altered," as applied to a composition, refers to an increase or decrease in the therapeutic effectiveness of the composition of at least about 20% or more as compared to the effectiveness of a composition consisting of the recited components.

The term "therapeutically effective amount" or "effective amount," as used herein, refers to that amount of a composition, compound, or agent of this invention that imparts a modulating effect, which, for example, can be a beneficial effect, to a subject afflicted with a disorder, disease or illness, including improvement in the condition of the subject (e.g., in one or more symptoms), delay or reduction in the progression of the condition, prevention or delay of the onset of the disorder, and/or change in clinical parameters, disease or illness, etc., as would be well known in the art. For example, a therapeutically effective amount or effective amount can refer to the amount of a composition, compound, or agent that improves a condition in a subject by at least 5%, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

"Treat" or "treating" or "treatment" refers to any type of action that imparts a modulating effect, which, for example, can be a beneficial effect, to a subject afflicted with a disorder, disease or illness, including improvement in the condition of the subject (e.g., in one or more symptoms), delay or reduction in the progression of the condition, and/or change in clinical parameters, disease or illness, etc., as would be well known in the art.

A "disorder amenable to treatment with APC" refers to any disorder in which administration of APC to a subject results in the treatment of one or more symptoms of the disorder in the subject. Examples of disorders are shown in the patents incorporated above.

"Pharmaceutically acceptable," as used herein, means a material that is not biologically or otherwise undesirable, i.e., the material can be administered to an individual along with the compositions of this invention, without causing substantial deleterious biological effects or interacting in a deleterious manner with any of the other components of the composition in which it is contained. The material would naturally be selected to minimize any degradation of the active ingredient and to minimize any adverse side effects in the subject, as would be well known to one of skill in the art (see, e.g., *Remington's Pharmaceutical Science;* $21^{st}$ ed. 2005).

"Concurrently" means sufficiently close in time to produce a combined effect (that is, concurrently can be simultaneously, or it can be two or more events occurring within a short time period before or after each other). In some embodiments, the administration of two or more compounds "concurrently" means that the two compounds are administered closely enough in time that the presence of one alters the biological effects of the other. The two compounds can be administered in the same or different formulations or sequentially. Concurrent administration can be carried out by mixing the compounds prior to administration, or by administering the compounds to the subject in two different formulations, for example, at the same point in time but at different anatomic sites or using different routes of administration.

The term "alkyl" denotes a straight or branched hydrocarbon chain containing 1-12 carbon atoms, e.g., 1-8, 1-6, or 1-4 carbon atoms. Examples of alkyl groups include methyl, ethyl, propyl, isopropyl, butyl, isobutyl, tert-butyl, and the like.

By "substituted alkyl" is meant an alkyl in which an atom of the alkyl is substituted with, for example, a carbon, nitrogen, sulfur, oxygen, silicon, or halogen atom, or alternatively a nitrogen, sulfur, oxygen, or halogen atom. The term encompasses substituents on alkyl, alkenyl, alkynyl, and cycloalkyl groups.

Examples of substituents that can be attached to any atom of the alkyl group in a "substituted alkyl" include cyclyl groups, heterocyclyl groups; aryl groups, heteroaryl groups, amino groups, amido groups, nitro groups, cyano groups, azide groups, hydroxy groups, alkoxy groups, acyloxy groups, thioalkoxy groups, acyl thioalkoxy groups, halogen groups, sulfonate groups, sulfonamide groups, ester groups, carboxylic acids, oxygen (e.g., a carbonyl group), and sulfur (e.g., a thiocarbonyl group). Substituents also include any chemical functional group that imparts improved water-solubility to the molecule (e.g., carboxylic acid, carboxylic ester, carboxamido, morpholino, piperazinyl, imidazolyl, thiomorpholino, or tetrazolyl groups; both unsubstituted and substituted).

The terms "halo" and "halogen" refer to any radical of fluorine, chlorine, bromine or iodine.

The term "alkoxy" denotes an oxygen linked to an alkyl or substituted alkyl as defined above.

The term "thioalkoxy" denotes a sulfur linked to an alkyl or substituted alkyl as defined above.

The term "cycloalkyl" denotes a monocyclic saturated carbocyclic group containing 3-8 carbon atoms, e.g., 3-6 carbon atoms. Examples of cycloalkyl groups include cyclopropyl, cyclobutyl, cyclopentyl, cyclohexyl, cycloheptyl, cyclooctyl, and the like.

The term "aryl" refers to an aromatic 5-8 membered monocyclic or 8-12 membered bicyclic ring system wherein 0, 1, 2, or 3 atoms of each ring can be substituted by a substituent. The term also includes aromatic bicyclic ring systems in which a hydrogen atom has been added to one, two, or three of the ring carbons in one of the rings (e.g., a partially saturated ring). Examples of aryl groups include phenyl, naphthyl and the like.

The term "arylalkyl" denotes an aryl group linked to an alkyl or substituted alkyl as defined above.

The term "heterocycle" refers to an aromatic or nonaromatic 5-8 membered monocyclic or 8-12 membered bicyclic ring system comprising 1-3 heteroatoms if monocyclic or 1-6 heteroatoms if bicyclic, said heteroatoms selected from O, N, or S, wherein 0, 1, 2 or 3 atoms of each ring can be substituted by a substituent. The term also includes aromatic and nonaromatic bicyclic ring systems in which a hydrogen atom has been added to one, two, or three of the ring carbons in one of the rings (e.g., a partially saturated ring). Examples of heterocycle groups include pyridyl, furyl or furanyl, benzofuranyl, imidazolyl, benzimidazolyl, pyrimidinyl, thiophenyl or thienyl, benzothiophenyl, quinolinyl, isoquinolinyl, dihydroquinolinyl, dihydroisoquinolinyl, naphthyridinyl, dihydronaphthyridinyl, quinazolinyl, indolyl, indazolyl, thiazolyl, benzothiazolyl, oxazinyl, benzooxazinyl, oxazolyl, benzooxazolyl, dihydrobenzodioxinyl, and the like.

Suitable substituents for aryl and heteroaryl groups are the same as the substituents for alkyl groups.

The present invention relates to the identification and characterization of analogs of APC that are expected to have equivalent or similar biological and therapeutic activity. The structure of APC free base is given below.

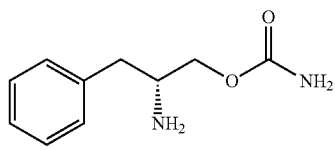

Thus, one aspect of the invention relates to a compound of Formula I:

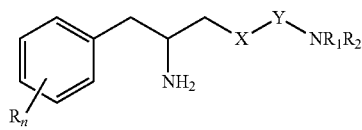

or a pharmaceutically acceptable salt thereof, wherein:
X is $CH_2$, O, NH, or S;
Y is C=O, C=S, or $SO_2$;
R is optionally substituted $C_{1-8}$ alkyl, halogen, optionally substituted $C_{1-4}$ alkoxy, cyano, hydroxy, optionally substituted trifluoromethyl, or $C_{1-4}$ thioalkoxy;
n is 0, 1, 2, or 3, with the proviso that R may be the same or different when x is 2 or 3; and
$R_1$ and $R_2$ can be the same or different and are independently selected from the group consisting of hydrogen, optionally substituted $C_{1-8}$ alkyl, optionally substituted amide, optionally substituted aryl, optionally substituted heteroaryl, optionally substituted arylalkyl, and optionally substituted $C_{3-7}$ cycloalkyl;
or $R_1$ and $R_2$ can be joined to form a 5 to 7-membered heterocycle optionally substituted with alkyl or aryl groups, wherein the cyclic compound can comprise 1 to 2 nitrogen atoms and 0 to 1 oxygen atom, wherein the nitrogen atoms are not directly connected with each other or with the oxygen atom;
wherein when Y is C=O, X is not O.

In some embodiments, X is $CH_2$, O, or NH; X is $CH_2$, O, or S; X is $CH_2$, NH, or S; X is O, NH, or S; X is $CH_2$ or S; X is $CH_2$ or NH; X is $CH_2$ or O; X is O or S; X is NH or S; X is O or S; X is O or NH; X is $CH_2$; X is O; X is NH; or X is S.

In some embodiments, Y is C=O or $SO_2$; Y is C=O or C=S; Y is C=S or $SO_2$; Y is C=O; Y is C=S; or Y is $SO_2$.

In some embodiments, $R_1$ or $R_2$ is $C(O)NR_3R_4$, wherein $R_3$ and $R_4$ are independently hydrogen, optionally substituted lower alkyl of 1 to 8 carbon atoms, optionally substituted aryl, optionally substituted arylalkyl, or optionally substituted cycloalkyl of 3 to 7 carbon atoms; or $R_3$ and $R_4$ can be joined to form a 5 to 7-membered heterocycle optionally substituted with a member selected from the group consisting of alkyl and aryl groups, wherein the heterocycle can comprise 1 to 2 nitrogen atoms and 0 to 1 oxygen atom, wherein the nitrogen atoms are not directly connected with each other or with the oxygen atom. In some embodiments, $R_1$ or $R_2$ is $C(O)NH_2$. See U.S. Application No. 62/404,917, the contents of which are incorporated by reference in their entirety, In some embodiments, the compound of Formula I has the structure of Formula Ia:

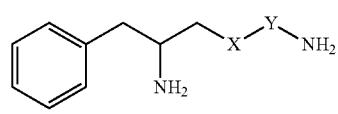

or a pharmaceutically acceptable salt thereof.

In some embodiments, the compound of Formula I has the structure of Formula II:

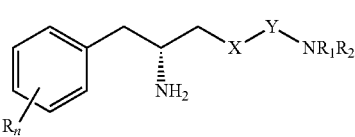

or a pharmaceutically acceptable salt thereof.

In certain embodiments, the compound of Formula II has the structure of Formula IIa:

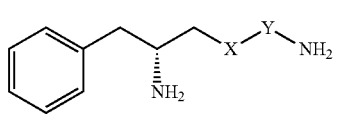

or a pharmaceutically acceptable salt thereof.

In some embodiments, the compound of Formula I has the structure of Formula III:

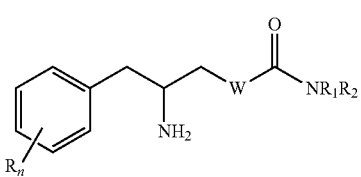

or a pharmaceutically acceptable salt thereof, wherein:
W is $CH_2$ or NH.

In certain embodiments, the compound of Formula III has the structure of Formula IIIa:

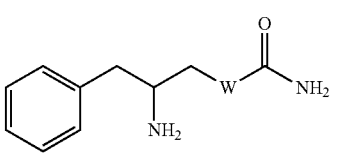

or a pharmaceutically acceptable salt thereof.

Examples of compounds within the structure of Formula IIIa include without limitation, compounds 1 and 2:

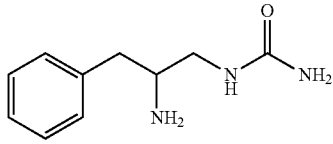

1

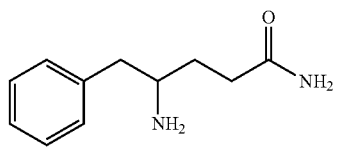

2 or a pharmaceutically acceptable salt thereof.

In some embodiments, the compound of Formula III has the structure of Formula IV:

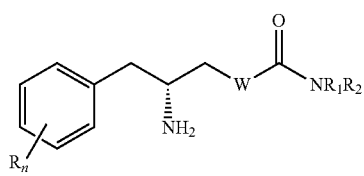

IV or a pharmaceutically acceptable salt thereof, wherein:
W is $CH_2$ or NH.

In certain embodiments, the compound of Formula IV has the structure of Formula IVa:

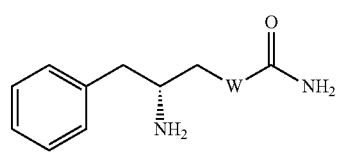

IVa or a pharmaceutically acceptable salt thereof, wherein:
W is $CH_2$ or NH.

Examples of compounds within the structure of Formula IVa include without limitation, compounds 3 and 4:

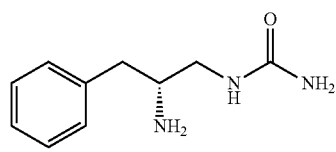 [SMILES: NC(=O)NC[C@H](N)Cc1ccccc1]

3

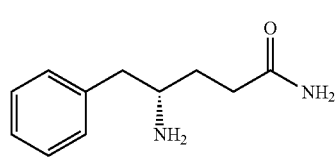 [SMILES: NC(=O)CC[C@H](N)Cc1ccccc1]

4 or a pharmaceutically acceptable salt thereof.

In some embodiments, the compound of Formula I has the structure of Formula V:

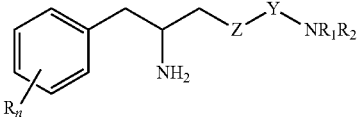

V or a pharmaceutically acceptable salt thereof, wherein:
Z is O or S; and
Y is C=O, C=S, or $SO_2$;
wherein when Y is C=O, Z is not O.

In certain embodiments, the compound of Formula V has the structure of Formula Va:

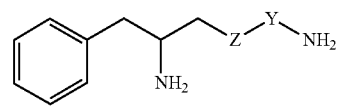

Va or a pharmaceutically acceptable salt thereof.

Examples of compounds within the structure of Formula IVa include without limitation, compounds 5, 6, and 7:

5

6

7 or a pharmaceutically acceptable salt thereof.

In some embodiments, the compound of Formula V has the structure of Formula VI:

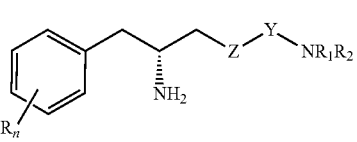

VI or a pharmaceutically acceptable salt thereof.

In certain embodiments, the compound of Formula VI has the structure of Formula VIa:

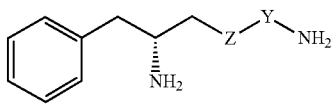

VIa or a pharmaceutically acceptable salt thereof.

Examples of compounds within the structure of Formula IVa include without limitation, compounds 8, 9, and 10:

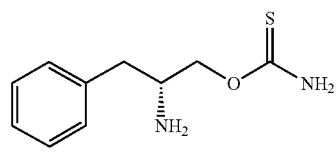 [SMILES: NC(=S)OC[C@H](N)Cc1ccccc1]

8

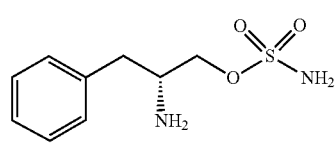 [SMILES: N[C@@H](COS(N)(=O)=O)Cc1ccccc1]

9

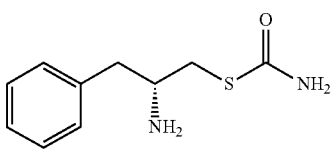 [SMILES: NC(=O)SC[C@H](N)Cc1ccccc1]

10 or a pharmaceutically acceptable salt thereof.

The compounds, formulations and unit dosage forms provided herein can be utilized, e.g., to achieve immediate, controlled, and/or delayed release of the compound of the invention, as well as pharmaceutically acceptable salts, hydrates, isomers, including tautomers, solvates and complexes of the compound.

Suitable salts of the compound of the invention include, without limitation, acetate, adipate, alginate, aspartate, benzoate, butyrate, citrate, fumarate, glycolate, hemisulfate, heptanoate, hexanoate, hydrochloride, hydrobromide, hydroiodide, 2-hydroxyethanesulfonate, lactate, maleate, malonate, methanesulfonate, nicotinate, nitrate, oxalate, palmoate, pectinate, persulfate, hydroxynapthoate, pivalate, propionate, salicylate, succinate, sulfate, tartrate, thiocyanate, tosylate and undecanoate. Other acids, such as oxalic, while not in themselves pharmaceutically acceptable, can be employed in the preparation of salts useful as intermediates in obtaining the compound of the invention and their pharmaceutically acceptable acid addition salts. In certain embodiments, the salt is the hydrochloride salt.

Compounds of the formulae herein include those having quaternization of any basic nitrogen-containing group therein.

The discussion herein is, for simplicity, provided without reference to stereoisomerism or the addition of deuterium atoms. Those skilled in the art will appreciate that the compound of the invention can contain one or more asymmetric centers and thus occur as racemates and racemic mixtures and single optical isomers. All such isomeric and deuterated forms of these compounds are expressly included in the present invention. In some embodiments, the compound is in the form of a single stereoisomer or a mixture in which one stereoisomer predominates, e.g., by about 60%, 70%, 80%, 90%, 95%, or more.

The discussion herein is also provided without reference to polymorphs, hydrates, clathrates, solvates, inclusion compounds, isomers, or other forms of the compound. All such forms of these compounds are expressly included in the present invention.

Further, the compounds of the invention include prodrugs of the compounds that are converted to the active compound in vivo. For example, the compound can be modified to enhance cellular permeability (e.g., by esterification of polar groups) and then converted by cellular enzymes to produce the active agent. Methods of masking charged or reactive moieties as a pro-drug are known by those skilled in the art (see, e.g., P. Korgsgaard-Larsen and H. Bundgaard, A Textbook of Drug Design and Development, Reading U.K., Harwood Academic Publishers, 1991).

The term "prodrug" refers to compounds that are rapidly transformed in vivo to yield the parent compound of the above formula, for example, by hydrolysis in blood, see, e.g., T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein. See also U.S. Pat. No. 6,680,299. Exemplary prodrugs include a prodrug that is metabolized in vivo by a subject to an active drug having an activity of the compounds as described herein, wherein the prodrug is an ester of an alcohol or carboxylic acid group, if such a group is present in the compound; an amide of an amine group or carboxylic acid group, if such groups are present in the compound; a urethane of an amine group, if such a group is present in the compound; an acetal or ketal of an alcohol group, if such a group is present in the compound; a N-Mannich base or an imine of an amine group, if such a group is present in the compound; or a Schiff base, oxime, acetal, enol ester, oxazolidine, or thiazolidine of a carbonyl group, if such a group is present in the compound, such as described, for example, in U.S. Pat. Nos. 6,680,324 and 6,680,322.

The term "pharmaceutically acceptable prodrug" (and like terms) as used herein refers to those prodrugs of the compound of the present invention which are, within the scope of sound medical judgment, suitable for use in contact with the tissues of humans and/or other animals without undue toxicity, irritation, allergic response and the like, commensurate with a reasonable risk/benefit ratio, and effective for their intended use, as well as the zwitterionic forms, where possible, of the compound of the invention.

The compound of the invention may be synthesized by methods known in the art and as disclosed in the examples.

Another aspect of the invention relates to a composition, e.g., a dosage form, comprising the compound of the invention. In some embodiments, the composition is a pharmaceutical composition comprising the compound of the invention and a pharmaceutically acceptable carrier. In some embodiments, the dosage form is an oral dosage form, e.g., a tablet or a capsule, e.g., an immediate release dosage form.

In some embodiments, the dosage form is an immediate release tablet that releases at least 85%, e.g., at least 85%, 90%, 95%, 96%, 97%, 98%, or 99%, of the compound of the invention contained therein within a period of less than 15 minutes after administration of the tablet to a subject.

Formulations of the compound of the invention, including immediate release formulations, may be processed into unit dosage forms suitable for oral administration, such as for example, filled capsules, compressed tablets or caplets, or other dosage form suitable for oral administration using conventional techniques. Immediate release dosage forms prepared as described may be adapted for oral administration, so as to attain and maintain a therapeutic level of the compound over a preselected interval. In certain embodiments, an immediate release dosage form as described herein may comprise a solid oral dosage form of any desired shape and size including round, oval, oblong cylindrical, or polygonal. In one such embodiment, the surfaces of the immediate release dosage form may be flat, round, concave, or convex. In some embodiments, the formulations may be the solid oral dosage forms described in U.S. Application No. 62/383,818, incorporated herein by reference in its entirety.

In particular, when the immediate release formulations are prepared as a tablet, the immediate release tablets contain a relatively large percentage and absolute amount of the compound and so are expected to improve patient compliance and convenience, by replacing the need to ingest large amounts of liquids or liquid/solid suspensions. One or more immediate release tablets as described herein can be administered, by oral ingestion, e.g., closely spaced, in order to provide a therapeutically effective dose of the compound to the subject in a relatively short period of time.

Where desired or necessary, the outer surface of an immediate release dosage form may be coated, e.g., with a color coat or with a moisture barrier layer using materials and methods known in the art.

Methods are disclosed herein to treat conditions amenable to treatment by APC, by administering an effective amount of one or more dosage forms as described herein. For example, the present dosage forms can be administered to treat a subject in need of treatment for narcolepsy, cataplexy, excessive daytime sleepiness, idiopathic hypersomnia, drug addiction, sexual dysfunction (e.g., hyposexual desire disorder), fatigue, fibromyalgia, attention deficit/hyperactivity disorder (ADHD) (e.g., treatment-resistant ADHD), restless legs syndrome, depression, bipolar disorder, atypical depression, binge eating disorder, or obesity in a subject in need thereof, or promoting smoking cessation in a subject in need thereof, thereby treating the disorder or condition or promoting smoking cessation. See, e.g., U.S. Pat. Nos. 8,232, 315; 8,440,715; 8,552,060; 8,623,913; 8,729,120; 8,741, 950; 8,895,609; 8,927,602; 9,226,910; 9,359,290; and 9,610,274; and U.S. Publication No. 2015/0018414; each of which is incorporated by reference in its entirety with respect to the disorder to be treated.

In certain embodiments, the excessive daytime sleepiness is associated with idiopathic hypersomnia, obstructive sleep apnea, multiple sclerosis, atypical depression, or drug-associated excessive sleepiness (DAES).

In certain embodiments, the fatigue is associated with multiple sclerosis, cancer or other conditions.

In some embodiments, the disorder or condition is multiple sclerosis, atypical depression, or DAES.

In some embodiments, the methods are used to improve cognition in a subject, e.g., a subject with mild cognitive impairment.

In certain embodiments, the compounds of the invention may treat multiple symptoms of a disorder. Examples include, without limitation, ADHD, where the compounds may improve excessive sleepiness and ADHD symptoms such as vigilance; atypical depression, where the compounds may improve excessive sleepiness and/or depressive symptoms; and multiple sclerosis, where the compounds may improve excessive sleepiness and/or fatigue.

The dosage forms disclosed herein can also be provided as a kit comprising, for example, separately packaged, a container comprising a plurality of immediate release tablets or capsules, which tablets or capsules can be individually packaged, as in foil envelopes or in a blister pack. The tablets or capsules can be packaged in many conformations with or without desiccants or other materials to prevent ingress of water. Instruction materials or means, such as printed labeling, can also be included for their administration, e.g., sequentially over a preselected time period and/or at preselected intervals, to yield the desired levels of the compound in vivo for preselected periods of time, to treat a preselected condition.

A daily dose of about 1 to about 2000 mg of the compound of the invention or a pharmaceutically acceptable salt thereof may be administered to accomplish the therapeutic results disclosed herein. For example, a daily dosage of about 10-1000 mg, e.g., about 20-500 mg, in single or divided doses, is administered. In some embodiments, the daily dose may be about 0.01 to about 150 mg/kg body weight, e.g., about 0.2 to about 18 mg/kg body weight.

In one embodiment of the invention, the compound of the invention is administered to the subject as needed to treat a disorder or condition. The compound can be administered continuously or intermittently. In one embodiment, the compound is administered to the subject more than once a day, e.g., 2, 3, or 4 times per day, or once every 1, 2, 3, 4, 5, 6, or 7 days. In another embodiment, the compound is administered to the subject no more than once a week, e.g., no more than once every two weeks, once a month, once every two months, once every three months, once every four months, once every five months, once every six months, or longer. In a further embodiment, the compound is administered using two or more different schedules, e.g., more frequently initially (for example to build up to a certain level, e.g., once a day or more) and then less frequently (e.g., once a week or less). In other embodiments, the compound can be administered by any discontinuous administration regimen. In one example, the compound can be administered not more than once every three days, every four days, every five days, every six days, every seven days, every eight days, every nine days, or every ten days, or longer. The administration can continue for one, two, three, or four weeks or one, two, or three months, or longer. Optionally, after a period of rest, the compound can be administered under the same or a different schedule. The period of rest can be one, two, three, or four weeks, or longer, according to the pharmacodynamic effects of the compound on the subject. In another embodiment the compound can be administered to build up to a certain level, then maintained at a constant level and then a tailing dosage.

In one aspect of the invention, the compound of the invention is delivered to a subject concurrently with an additional therapeutic agent. The additional therapeutic agent can be delivered in the same composition as the compound or in a separate composition. The additional therapeutic agent can be delivered to the subject on a different schedule or by a different route as compared to the compound. The additional therapeutic agent can be any agent that provides a benefit to the subject. Further agents include, without limitation, stimulants, anti-psychotics, anti-depressants, agents for neurological disorders, and chemotherapeutic agents. One therapeutic agent that can be administered during the same period is Xyrem®, sold commercially by Jazz Pharmaceuticals, which is used to treat narcolepsy and cataplexy. See U.S. Pat. Nos. 8,952,062 and 9,050,302.

The present invention finds use in research as well as veterinary and medical applications. Suitable subjects are generally mammalian subjects. The term "mammal" as used herein includes, but is not limited to, humans, non-human primates, cattle, sheep, goats, pigs, horses, cats, dog, rabbits, rodents (e.g., rats or mice), etc. Human subjects include neonates, infants, juveniles, adults and geriatric subjects.

In particular embodiments, the subject is a human subject that has a disorder amenable to treatment with APC. In other embodiments, the subject used in the methods of the invention is an animal model of a disorder amenable to treatment with APC.

The subject can be a subject "in need of" the methods of the present invention, e.g., in need of the therapeutic effects of the inventive methods. For example, the subject can be a subject that is experiencing a disorder amenable to treatment with APC, is suspected of having a disorder amenable to treatment with APC, and/or is anticipated to experience a disorder amenable to treatment with APC, and the methods and compositions of the invention are used for therapeutic and/or prophylactic treatment.

The present invention is explained in greater detail in the following non-limiting Examples.

Example 1

Synthesis of Compounds

Compound 8 (110CR002)

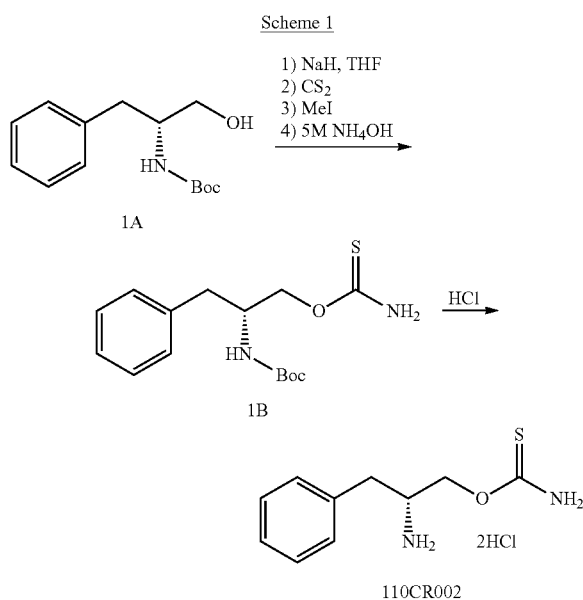

tert-Butyl (R)-(1-(Carbamothioyloxy)-3-phenylpropan-2-yl)carbamate (1B): A 60% dispersion of sodium hydride (0.36 g, 4.78 mmol, 1.2 equiv) in mineral oil was added in portions to compound 1A (1.0 g. 3.98 mmol, 1 equiv) in THF (20 mL) at 0° C. After stirring for 1 hour, carbon disulfide (0.191 g, 4.78 mmol, 1.2 equiv) was added at 0° C. After an additional hour of stirring, methyl iodide (0.3 mL, 4.78 mmol, 1.2 equiv) was added and the reaction was warmed to room temperature. After stirring two additional hours, concentrated ammonium hydroxide (1.6 mL, 7.98 mmol, 2 equiv) was added and the reaction was stirred overnight at room temperature. The reaction was diluted with water (50 mL) and extracted with dichloromethane (3×50 mL). The combined organic layers were dried over sodium sulfate and concentrated under reduced pressure to give crude compound 1B. The solid was triturated in diethyl ether (20 mL) to give compound 1B (0.17 g, 14% yield) as a light yellow solid.

(R)—O-(2-Amino-3-phenylpropyl) carbamothioate dihydrochloride (110CR002): 4M HCl in dioxane (0.68 mL, 2.74 mmol, 5 equiv) was added to neat compound 1B (0.17 g, 0.548 mmol, 1 equiv) and the reaction was stirred overnight. The solution was diluted with diethyl ether (20 mL) and the resulting suspension was filtered. The solid was triturated in diethyl ether (20 mL) and the filtered solid was dried under vacuum at room temperature for two hours to give compound 110CR003 (140 mg, 93% yield, 96.9% purity) as a white solid.

Compound 9 (110CR003)

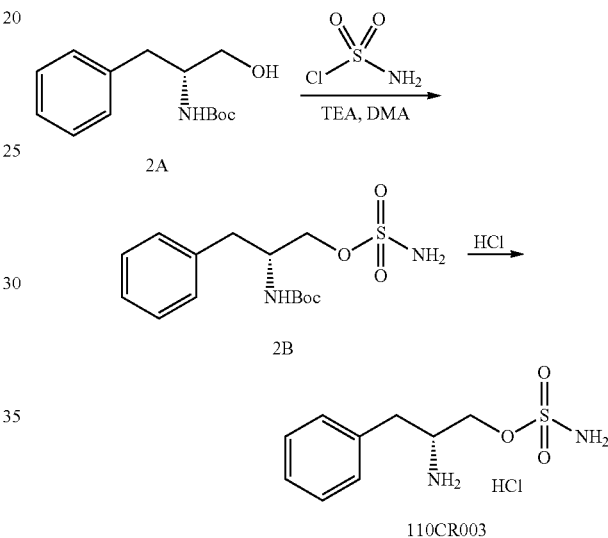

(R)-2-((tert-Butoxycarbonyl)amino)-3-phenylpropyl sulfamate (2B): A solution of sulfamoyl chloride (1.15 g, 9.95 mmol, 2.5 equiv) in acetonitrile (2 mL) was added dropwise to a solution of compound 2A (1.0 g, 3.98 mmol, 1 equiv) and triethylamine (2.1 mL, 14.95 mmol, 3.75 equiv) in N,N-dimethylacetamide (20 mL) at 0° C. After stirring at room temperature for 4 hours, additional triethylamine (2.1 mL, 14.95 mmol, 3.75 equiv) and sulfamoyl chloride (1.15 g, 9.95 mmol, 2.5 equiv) in acetonitrile (2 mL) was added at 0° C. The reaction was stirred at room temperature overnight, at which point LCMS indicated a 3:2 mixture of product to starting material. Additional triethylamine (2.1 mL, 14.95 mmol, 3.75 equiv) and sulfamoyl chloride (1.15 g, 9.95 mmol, 2.5 equiv) in acetonitrile (2 mL) was added at 0° C. and the reaction was stirred at room temperature for an additional 6 hours. LCMS indicated a 4:1 mixture of product to starting material. The reaction was quenched with saturated sodium bicarbonate (5 mL) and stirred for an additional hour at room temperature. The reaction was diluted with saturated sodium bicarbonate (25 mL) and extracted with ethyl acetate (3×50 mL). The combined organic layers were dried over sodium sulfate and concentrated under reduced pressure. The product still contained unreacted starting material which could not be easily separated. Sulfamoyl chloride (1.15 g, 9.95 mmol, 2.5 equiv) in acetonitrile (2 mL) was added dropwise to a solution of crude compound 2B (0.9 g) and triethylamine (2.1 mL, 14.95 mmol, 3.75 equiv) in N,N-dimethylacetamide (20 mL) at 0° C. After stirring at room temperature for two hours, the reaction was quenched with saturated sodium bicarbonate (5 mL) and the reaction was stirred for an additional hour at room temperature. The reaction was diluted with saturated sodium bicarbonate (25 mL) and extracted with ethyl acetate (3×50 mL). The combined organic layers were dried over sodium sulfate and concentrated under reduced pressure. The residue was purified on an AnaLogix automated system (Redisep 24 g silica gel column), eluting with a gradient of 25 to 50% ethyl acetate in heptanes, to give compound 2B (0.37 g, 28% yield) as a white solid.

(R)-2-Amino-3-phenylpropyl sulfamate hydrochloride (110CR003): 4M HCl in dioxane (1.4 mL, 5.6 mmol, 5 equiv) was added to neat compound 2B (0.37 g, 1.12 mmol, 1 equiv) and the reaction was stirred overnight. The solution was diluted with diethyl ether (20 mL) and the resulting suspension was filtered. The solid was triturated in diethyl ether (20 mL) and the filtered solid was dried under a vacuum at room temperature for two hours to give compound 110CR003 (250 mg, 84% yield, 97.8% purity) as a white solid.

Compound 3 (110CR007)

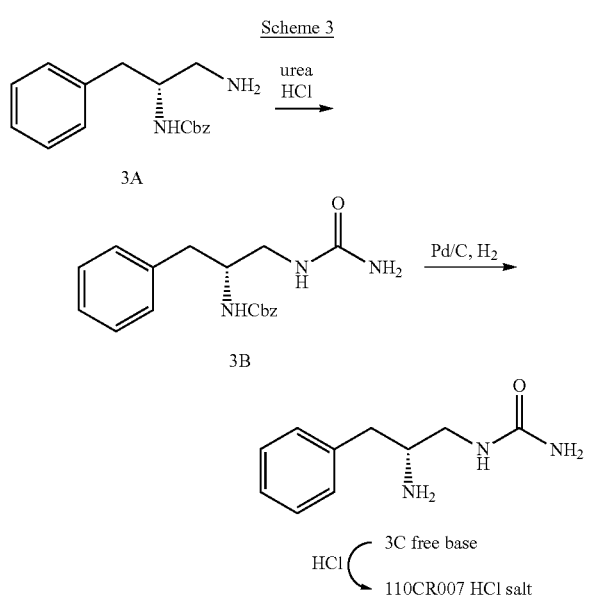

Scheme 3

(Benzyl (R)-(1-phenyl-3-ureidopropan-2-yl)carbamate) (3B): Concentrated hydrochloric acid (0.06 mL, 0.68 mmol, 0.12 equiv) was added to a solution of benzyl (R)-(1-amino-3-phenylpropan-2-yl)carbamate (1.5 g, 5.28 mmol, 1 equiv) and urea (1.26 g, 21.21 mmol, 4 equiv) in toluene (150 mL) under nitrogen. After refluxing overnight, LCMS indicated the reaction was complete. The reaction was concentrated under reduced pressure, diluted with water (150 mL) and stirred for 30 minutes. The resulting solid was filtered and washed with water (25 mL) to give crude compound 3B (1.4 g, 4.27 mmol, 80% yield) as a white solid, which was used sequentially.

((R)-1-(2-mino-3-phenylpropyl)urea) (3C): Compound 3B (0.5 g, 1.5 mmol, 1 equiv) and 10% palladium on carbon (0.09 g) in methanol (60 mL) was hydrogenated at 30 psi for 1 hour at which time LC-MS determined that the reaction was incomplete. The solution was filtered and fresh catalyst (0.09 g) was added. The solution was hydrogenated at 30 psi for an additional 45 minutes resulting in complete conversion. Two identical scale reactions were run for 105 minutes each, both resulting in complete conversion. The three runs were combined and filtered through celite, which was washed with methanol (50 mL). The filtrate was concentrated under reduced pressure to give crude compound 3C (0.9 g), which was used sequentially.

(R)-1-(2-Amino-3-phenylpropyl)urea hydrochloride (110CR007): Compound 3C (0.88 g, 4.58 mmol, 1 equiv) was dissolved diethyl ether (10 mL) and 4 N HCl in dioxane (2.31 mL, 9.27 mmol, 2 equiv) was added. The reaction was stirred overnight and then concentrated under reduced pressure to give crude 110CR007 as a white solid. The material was twice recrystallized from 10% methanol in ethanol (30 mL) to give 110CR007 (0.163 g, 16% yield, 93.7% purity) as a white solid.

Compound 4 (110CR009)

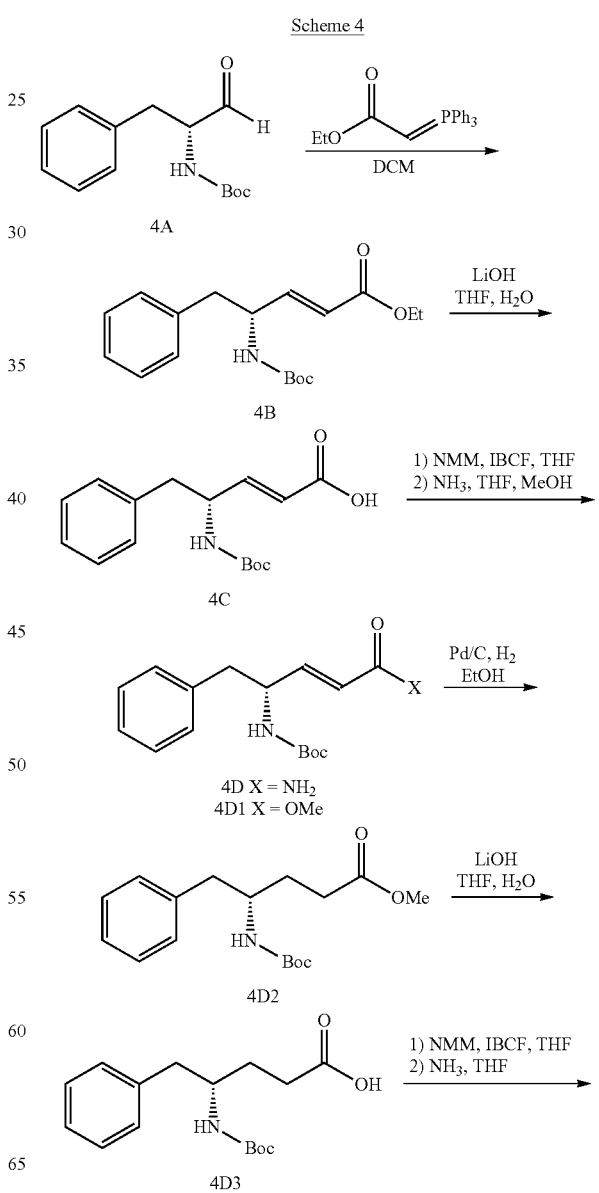

Scheme 4

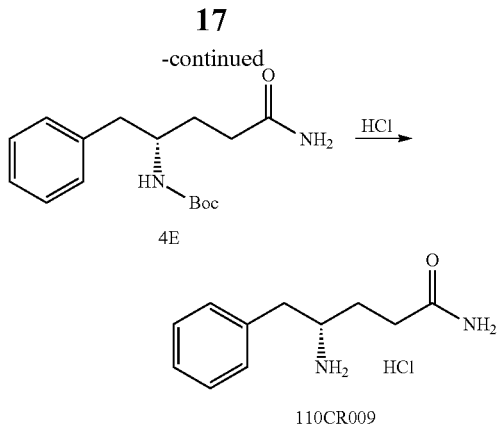

4E

110CR009

Ethyl (R,E)-4-((tert-butoxycarbonyl)amino)-5-phenyl-pent-2-enoate (4B): A solution of compound 4A (4.0 g, 16.1 mmol, 1 equiv) and ethyl (triphenylphos-phoranylidene) acetate (5.6 g, 16.1 mmol, 1 equiv) in dichloromethane (40 mL) was stirred at room temperature overnight. The reaction was concentrated under reduce pressure to remove the organic solvent and the resulting residue was purified on an AnaLogix automated system (40 g Sorbtech silica gel column), eluting with gradient of 50 to 100% ethyl acetate in heptanes, to give compound 4B (4.8 g, 94% yield) as a white solid.

(R,E)-4-((tert-Butoxycarbonyl)amino)-5-phenylpent-2-enoic acid (4C): Lithium hydroxide (1.4 g, 60 mmol, 4 equiv) in water (15 mL) was added to compound 4B (4.8 g, 15 mmol, 1 equiv) in THF (60 mL) at room temperature and the reaction was stirred overnight. After 16 hours, the reaction was adjusted to pH 4 with 1N hydrochloric acid. The organic layer was removed and the aqueous layer was extracted with ethyl acetate (2×50 mL). The combined organic layers was washed with saturated brine (50 mL), dried over sodium sulfate and concentrated under reduced pressure to give compound 4C (4.2 g, 97% yield) as a light cream solid, which was used subsequently.

Methyl (R,E)-4-((tert-butoxycarbonyl)amino)-5-phenyl-pent-2-enoate (4D1): Isobutyl chloroformate (1.3 mL, 10 mmol, 1 equiv) in THF (4 mL) was added dropwise to a solution of compound 4C (3.0 g, 10 mmol, 1 equiv) and N-methyl-morpholine (1.1 mL, 10 mmol, 1 equiv) in THF (12 mL) at −15° C. After 30 minutes of stirring, LCMS indicated complete conversion to the anhydride intermediate. 2M Ammonia in methanol (5 mL, 10 mmol, 1 equiv) was added dropwise over 20 minutes, keeping the internal temperature between −25 to −15° C. After 30 minutes of stirring, the reaction was warmed to room temperature and stirred overnight. The reaction mixture was concentrated at reduced pressure to remove the organic solvent. The resulting residue was dissolved in ethyl acetate (50 mL) and washed with water (100 mL). The aqueous layer was extracted with ethyl acetate (2×50 mL). The combined organic layers were washed with saturated brine (50 mL), dried over sodium sulfate and concentrated under reduced pressure. The residue was purified on an AnaLogix automated system (80 g Sorbtech silica gel column), eluting with a gradient of 25 to 50% ethyl acetate in heptanes, to give compound 4D1 (1.1 g, 35% yield) as a white solid.

Methyl (S)-4-((tert-butoxycarbonyl)amino)-5-phenylpen-tanoate (4D2): A mixture of compound 4D1 (1.1 g, 3.6 mmol, 1 equiv) and 10% palladium on carbon (0.33 g, 50% wet) in methanol (40 mL) was hydrogenated at 40 psi at room temperature for 4 hours. The mixture was filtered through celite, which was washed with methanol (100 mL). The filtrate was concentrated under reduced pressure to give compound 4D2 (1.1 g, 99% yield) as a white solid.

(S)-4-((tert-Butoxycarbonyl)amino)-5-phenylpentanoic acid (4D3): Lithium hydroxide (73 mg, 3 mmol, 1.5 equiv) in water (1 mL) was added to compound 4B (0.6 g, 2 mmol, 1 equiv) in THF (9 mL) at room temperature. After stirring overnight, the reaction was adjusted to pH 4 with 1N hydrochloric acid. The organic layer was removed and the aqueous layer was extracted with ethyl acetate (3×25 mL). The combined organic layers was washed with saturated brine (25 mL), dried over sodium sulfate and concentrated under reduced pressure to give compound 4D3 (0.56 g, 98% yield) as a white solid, which was used subsequently.

tert-Butyl (S)-(5-amino-5-oxo-1-phenylpentan-2-yl)car-bamate (4E): Isobutyl chloroformate (0.23 mL, 1.8 mmol, 1 equiv) in THF (0.5 mL) was added drop-wise to a solution of compound 4C (0.54 g, 1.8 mmol, 1 equiv) and N-meth-ylmorpholine (0.2 mL, 1.8 mmol, 1 equiv) in THF (1 mL) at −15° C. After 20 minutes of stirring, LCMS indicated complete conversion to the anhydride intermediate. 0.4M Ammonia in THF (9 mL, 3.6 mmol, 2 equiv) was added drop-wise over 20 minutes, keeping the internal temperature between −25 to −15° C. After 30 minutes of stirring the reaction was warmed to room temperature and stirred overnight. The reaction mixture was concentrated under reduced pressure to remove the organic solvent. The resulting residue was dissolved in ethyl acetate (25 mL) and washed with water (25 mL). The organic layer was separated and the aqueous layer was extracted with ethyl acetate (2×25 mL). The combined organic layers were washed with saturated brine (50 mL), dried over sodium sulfate and concentrated under reduced pressure to give compound 4E (0.5 g, 93% yield) as a white solid, which was used subsequently.

(S)-4-Amino-5-phenylpentanamide hydrochloride (110CR009): 4M HCl in dioxane (6 mL, 25 mmol, 10 equiv) was added to compound 4E (0.73 g, 1.12 mmol, 1 equiv). After stirring overnight at room temperature, the reaction was diluted with diethyl ether (20 mL) and stirred for 6 hours. The resulting suspension was filtered and the solid was washed with diethyl ether (20 mL). The filtered solid was dried under vacuum at room temperature for two hours to give compound 110CR009 (340 mg, 60% yield, 97.9% purity) as a white solid.

Compound 10 (110CR012)

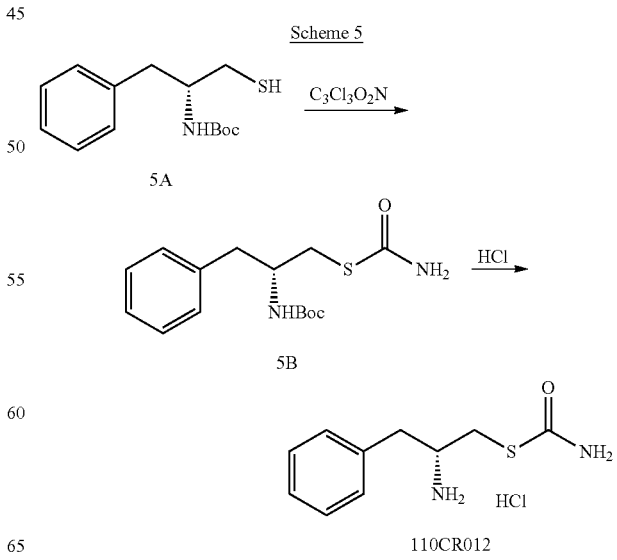

tert-Butyl (R)-(1-(carbamoylthio)-3-phenylpropan-2-yl) carbamate (5B): Compound 5A (0.15 g, 0.56 mmol, 1 equiv) was dissolved in THF (8 mL) and sparged with nitrogen for 15 minutes. Trichloroacetyl isocyanate (0.1 mL, 0.84 mmol, 1.5 equiv) was added and the solution stirred for 3 hours, at which point TLC (30% ethyl acetate in heptane) indicated absence of starting material. The reaction was cooled to 0° C. and concentrated ammonium hydroxide (0.15 mL) was added. After stirring overnight at room temperature, TLC indicated that the reaction was complete. The reaction was washed with a 10% ammonium hydroxide (10 mL). The organic layer was concentrated under reduced pressure. The residue was purified on an AnaLogix automated system (12 g silica gel column), eluting with a gradient of 0 to 30% ethyl acetate in heptane, to give compound 5B. This reaction was repeated an additional two times 0.15 g and 0.18 g). The products were to give compound 5B (0.35 g, 1.12 mmol, 62.2% yield) as a white solid.

(R)—S-(2-Amino-3-phenylpropyl) carbamothioate hydrochloride (110CR012): Compound 5B (0.35 g, 1.12 mmol, 1 equiv) was dissolved in 4N HCl in dioxane (2 mL). The reaction was stirred for two hours and then concentrated under reduced pressure to give crude 110CR012 as a white solid. The material was triturated in diethyl ether (15 mL) to give 110CR012 (0.215 g, 78% yield, 98.0% purity) as a white solid.

Example 2

Characterization of Binding Profile

Compounds of the invention were tested for pharmacological activity in comparison to APC. Eight binding assays were carried out to provide a binding profile for each compound, including binding to dopamine transporter (DAT), norepinephrine transporter (NET), serotonin (5-HT) transporter (SERT), alpha2A adrenergic receptor (Alpha2A), alpha2C adrenergic receptor (Alpha2C), D2S dopamine receptor (D2S), D2L dopamine receptor (D2L), and vesicular monoamine transporter (VMAT2). Competitive binding assays using a radiolabeled ligand were carried out with each compound at 10 μM. The radioligand for each target was as follows: DAT—BTCP, NET—nisoxetine, SERT—imipramine, Alpha2A—yohimbine, Alpha2C—yohimbine, D2S—7-OH-DPAT, D2L—methylspiperone, VMAT2—tetrabenazine. The source of the receptors and transporters were prepared cell membrane fractions. Assay conditions are shown in Table 1.

Results are shown in Table 2. Individual results are shown in Table 3. The similarity in binding profiles of APC and compound 3 and 4 (substantial binding to the dopamine transporter, minimal binding to other receptors and transporters) is indicative of similar biological activity. Compounds 8, 9, and 10, in addition to having substantial dopamine transporter binding activity, exhibit substantial binding to adrenergic and dopaminergic receptors and the norepinephrine transporter. This suggests, that these compounds may be useful for the same methods for which APC is useful and may also have additional therapeutic activities.

The foregoing is illustrative of the present invention, and is not to be construed as limiting thereof. The invention is defined by the following claims, with equivalents of the claims to be included therein. All publications, patent applications, patents, patent publications, and any other references cited herein are incorporated by reference in their entireties for the teachings relevant to the sentence and/or paragraph in which the reference is presented.

TABLE 1

| Assay | Source | Ligand | Conc. | Kd | Non-specific | Incubation | Detection method |
|---|---|---|---|---|---|---|---|
| Receptors | | | | | | | |
| $\alpha_{2A}$ (antagonist radioligand) | Human recombinant (CHO cells) | [$^3$H]RX 821002 | 1 nM | 0.8 nM | (−)epinephrine (100 μM) | 60 min RT | Scintillation counting |
| $\alpha_{2C}$ (antagonist radioligand) | Human recombinant (CHO cells) | [$^3$H]RX 821002 | 2 nM | 0.95 nM | (−)epinephrine (100 μM) | 60 min RT | Scintillation counting |
| $D_{2S}$ (agonist radioligand) | Human recombinant (HEK-293 cells) | [$^3$H]7-OH-DPAT | 1 nM | 0.68 nM | butaclamol (10 μM) | 60 min RT | Scintillation counting |
| $D_{2L}$ (antagonist radioligand) | Human recombinant (HEK-293 cells) | [$^3$H]methyl-spiperone | 0.3 nM | 0.1 nM | butaclamol (10 μM) | 60 min RT | Scintillation counting |
| Transporters | | | | | | | |
| Norepinephrine transporter (antagonist radioligand) | Human recombinant (CHO cells) | [$^3$H]nisoxetine | 1 nM | 2.9 nM | Desipramine (1 μM) | 120 min 4° C. | Scintillation counting |
| Dopamine transporter (antagonist radioligand) | Human recombinant (CHO cells) | [$^3$H]BTCP | 4 nM | 4.5 nM | BTCP (10 μM) | 120 min 4° C. | Scintillation counting |
| 5-HT transporter (antagonist radioligand) | Human recombinant (CHO cells) | [$^3$H]imipramine | 2 nM | 1.7 nM | imipramine (10 μM) | 60 min RT | Scintillation counting |
| VMAT2 transporter (antagonist radioligand) | Rat brain (minus cerebellum) | [$^3$H]dihydrotetra benazine | 10 nM | 14.0 nM | Ro-4-1284 (10 μM) | 30 min RT | Scintillation counting |

TABLE 2

Binding profile

| Compound* | Structure | % Inhibition of Binding at Each Transporter or Receptor Target | | | | | | | |
|---|---|---|---|---|---|---|---|---|---|
| | | Alpha2A | Alpha2C | D2S | D2L | NET | DAT | SERT | VMAT2 |
| APC | phenyl-CH2-CH(NH2)-CH2-O-C(=O)-NH2 | 7.0 | 3.2 | 4.4 | 2.3 | 11.4 | 80.2 | −4.8 | 7.0 |
| 3 | phenyl-CH2-CH(NH2)-CH2-NH-C(=O)-NH2 | 4.8 | 15.6 | −0.7 | 0.5 | 32.8 | 88.6 | −1.4 | 0.0 |
| 4 | phenyl-CH2-CH(NH2)-CH2-CH2-C(=O)-NH2 | −0.8 | 2.9 | −6.0 | 1.1 | −7.5 | 56.5 | −0.5 | 0.0 |
| 8 | phenyl-CH2-CH(NH2)-CH2-O-C(=S)-NH2 | 60.6 | 48.8 | 27.4 | 1.1 | 37.8 | 81.6 | −2.1 | 6.0 |
| 9 | phenyl-CH2-CH(NH2)-CH2-O-S(=O)2-NH2 | 68.3 | 63.4 | 39.5 | −4.5 | 5.1 | 35.2 | −2.7 | 16.0 |
| 10 | phenyl-CH2-CH(NH2)-CH2-S-C(=O)-NH2 | 55.3 | 90.9 | 90.0 | 34.7 | 91.7 | 86.3 | 21.9 | 5.0 |

*In the form of the hydrochloride salt.

TABLE 3

| | % inhibition of control specific binding | | |
|---|---|---|---|
| Compound | $1^{st}$ | $2^{nd}$ | Mean |
| $\alpha_{2A}$ (antagonist radioligand) | | | |
| APC | 5.2 | 8.7 | 7.0 |
| 3 | 1.7 | 7.8 | 4.8 |
| 4 | 7.8 | −9.3 | −0.8 |
| 8 | 60.0 | 61.3 | 60.6 |
| 9 | 65.7 | 70.8 | 68.3 |
| 10 | 64.4 | 46.1 | 55.3 |
| $\alpha_{2C}$ (antagonist radioligand) | | | |
| APC | 4.1 | 2.3 | 3.2 |
| 3 | 8.6 | 22.6 | 15.6 |
| 4 | 3.4 | 2.3 | 2.9 |
| 8 | 50.6 | 47.0 | 48.8 |
| 9 | 65.8 | 60.9 | 63.4 |
| 10 | 89.3 | 92.4 | 90.9 |

TABLE 3-continued

| | % inhibition of control specific binding | | |
|---|---|---|---|
| Compound | $1^{st}$ | $2^{nd}$ | Mean |
| $D_{2S}$ (agonist radioligand) | | | |
| APC | 0.7 | 8.2 | 4.4 |
| 3 | −1.6 | 0.2 | −0.7 |
| 4 | −8.2 | −3.7 | −6.0 |
| 8 | 33.5 | 21.4 | 27.4 |
| 9 | 45.3 | 33.7 | 39.5 |
| 10 | 89.5 | 90.5 | 90.0 |
| $D_{2L}$ (antagonist radioligand) | | | |
| APC | −0.1 | 4.6 | 2.3 |
| 3 | −6.7 | 7.6 | 0.5 |
| 4 | 1.4 | 0.8 | 1.1 |
| 8 | −0.5 | 2.7 | 1.1 |
| 9 | −2.2 | −6.8 | −4.5 |
| 10 | 33.7 | 35.6 | 34.7 |

TABLE 3-continued

| | % inhibition of control specific binding | | |
|---|---|---|---|
| Compound | $1^{st}$ | $2^{nd}$ | Mean |
| Norepinephrine transporter (antagonist radioligand) | | | |
| APC | 6.9 | 16.0 | 11.4 |
| 3 | 42.6 | 23.0 | 32.8 |
| 4 | 7.0 | −21.9 | −7.5 |
| 8 | 29.5 | 46.1 | 37.8 |
| 9 | −3.7 | 14.0 | 5.1 |
| 10 | 91.7 | 91.7 | 91.7 |
| Dopamine transporter (antagonist radioligand) | | | |
| APC | 79.3 | 81.1 | 80.2 |
| 3 | 86.8 | 90.5 | 88.6 |
| 4 | 52.9 | 60.0 | 56.5 |
| 8 | 67.9 | 95.4 | 81.6 |
| 9 | 26.4 | 44.0 | 35.2 |
| 10 | 85.3 | 87.3 | 86.3 |
| 5-HT transporter (antagonist radioligand) | | | |
| APC | −6.3 | −3.3 | −4.8 |
| 3 | −2.4 | −0.4 | −1.4 |
| 4 | −2.9 | 1.8 | −0.5 |
| 8 | −1.9 | −2.4 | −2.1 |
| 9 | −1.7 | −3.7 | −2.7 |
| 10 | 21.7 | 22.0 | 21.9 |
| VMAT2 transporter (antagonist radioligand) | | | |
| APC | 7 | | |
| 3 | 0 | | |
| 4 | 0 | | |
| 8 | 6 | | |
| 9 | 16 | | |
| 10 | 5 | | |

What is claimed is:

1. A compound of Formula V:

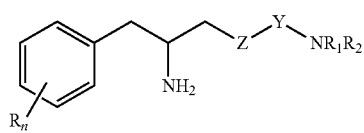

or a pharmaceutically acceptable salt thereof, wherein:
Z is S;
Y is C=S or $SO_2$;
R is optionally substituted $C_{1-8}$ alkyl, halogen, optionally substituted $C_{1-4}$ alkoxy, cyano, hydroxy, optionally substituted trifluoromethyl, or $C_{1-4}$ thioalkoxy;
n is 0, 1, 2, or 3, with the proviso that R may be the same or different when n is 2 or 3; and
$R_1$ and $R_2$ can be the same or different and are independently selected from the group consisting of hydrogen, optionally substituted $C_{1-8}$ alkyl, optionally substituted amide, optionally substituted aryl, optionally substituted heteroaryl, optionally substituted arylalkyl, and optionally substituted $C_{3-7}$ cycloalkyl;
or $R_1$ and $R_2$ can be joined to form a 5 to 7-membered heterocycle optionally substituted with alkyl or aryl groups, wherein the cyclic compound can comprise 1 to 2 nitrogen atoms and 0 to 1 oxygen atom, wherein the nitrogen atoms are not directly connected with each other or with the oxygen atom.

2. The compound of claim 1, having Formula Va:

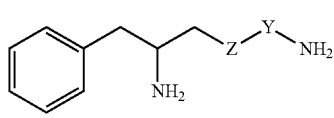

or a pharmaceutically acceptable salt thereof.

3. The compound of claim 1, having Formula VIa:

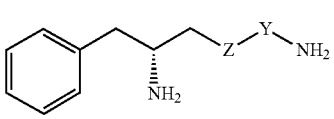

or a pharmaceutically acceptable salt thereof.

4. The compound of claim 1, which is the hydrochloride salt.

5. A composition comprising the compound of claim 1.

6. A pharmaceutical composition comprising the compound of claim 1 and a pharmaceutically acceptable carrier.

7. The composition of claim 6, wherein the composition is a dosage form.

8. The composition of claim 7, wherein the composition is an immediate release oral dosage form.

9. The composition of claim 8, wherein the composition is a tablet or a capsule.

10. A kit comprising the compound of claim 1.

11. The compound of claim 1, wherein $R_1$ and $R_2$ are hydrogen.

12. The compound of claim 1, wherein n is 0.

* * * * *